Figure 1:
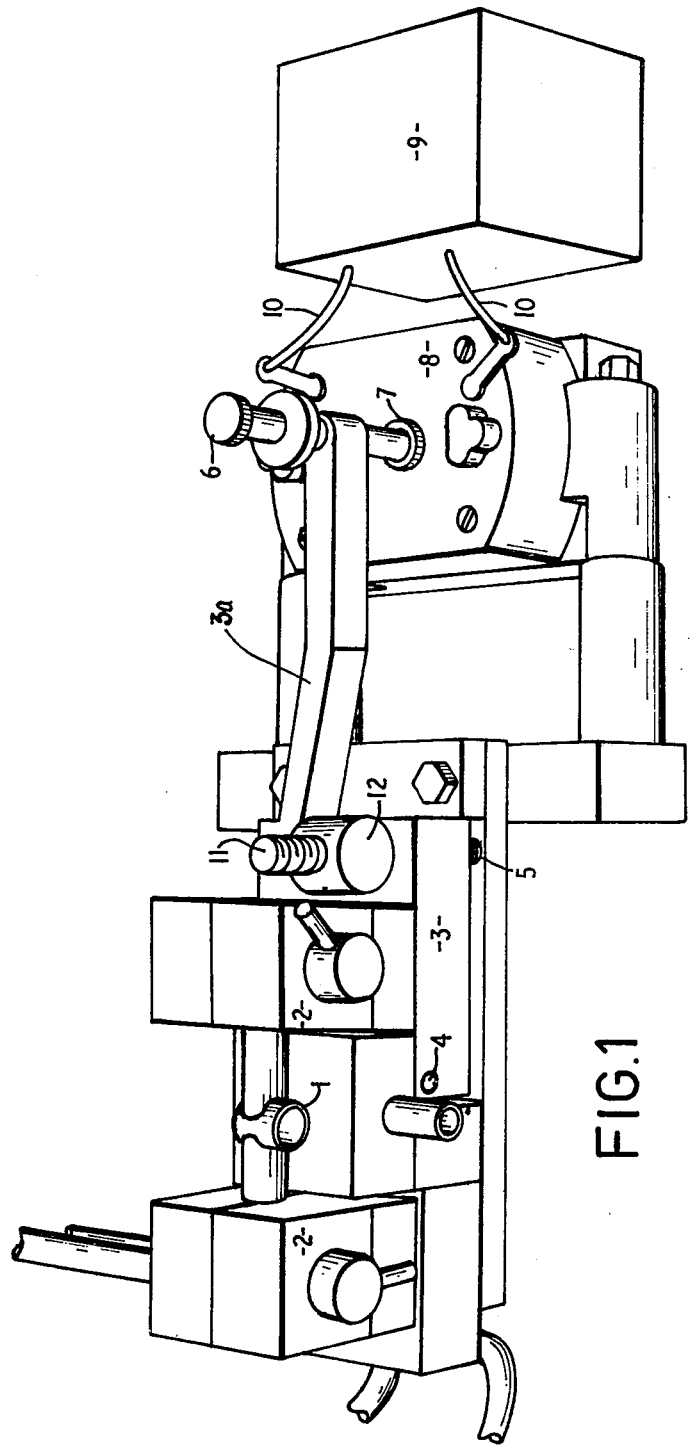

United States Patent [19]

Smythe et al.

[11] 4,181,438

[45] Jan. 1, 1980

[54] DIRECT TEMPERATURE CONTROL AND MEASUREMENT FOR FURNACE ATOMIZERS IN ATOMIC SPECTROSCOPY

[76] Inventors: Lloyd E. Smythe, 7 Aston Gardens, Bellevue Hill, New South Wales; Jaroslav P. Matousek, 77 Brown St., Forestville, New South Wales, both of Australia

[21] Appl. No.: 846,326

[22] Filed: Oct. 28, 1977

[30] Foreign Application Priority Data

Feb. 10, 1977 [AU] Australia ............................. PC9027

[51] Int. Cl.² .............................................. G01J 3/30
[52] U.S. Cl. ...................................... 356/312; 73/363
[58] Field of Search .................. 356/74, 85, 312, 300; 73/363

[56] References Cited
PUBLICATIONS

"New Methods for Programmed Heating of Electrically Heated Nonflame Atomic Vapor Cells", Montaser et al.; Analytical Chemistry, vol. 47, #1, pp. 38–45, Jan. 1975.

"Simple & Reliable Furnace Temp. Control System", Morrow et al.; J. Sci. Instrum., 1962, vol. 39, p. 34.

Primary Examiner—Vincent P. McGraw
Attorney, Agent, or Firm—Irvin A. Lavine

[57] ABSTRACT

Apparatus for directly controlling the power delivered to an electrically heated furnace atomizer for use in atomic spectroscopy and thus for controlling the temperature of the furnace by utilizing dimensional changes produced in the furnace due to thermal expansion and contraction to produce electrical signals that are used by means of a feedback control to control the electrical input to the furnace.

2 Claims, 2 Drawing Figures

DIRECT TEMPERATURE CONTROL AND MEASUREMENT FOR FURNACE ATOMIZERS IN ATOMIC SPECTROSCOPY

The present invention relates to a method of and to an apparatus for measuring and controlling the temperature of furnace atomizers in atomic spectroscopy.

Furnace atomizers are usually made of graphite and are designed to convert solid or liquid samples into atomic vapour by heating to high temperatures. Atomic absorption, fluorescence or emission signals due to the atomic vapour may be related to the concentration of the analyte element in the original sample by means of well-known formulae.

Furnace atomizers have been reviewed extensively for example by Syty (1974) pages 211 to 288.

A furnace atomizer may be heated in a sequence of drying, ashing (charring) and atomization, by applying preselected voltages for preselected times by means of a suitably constructed power supply.

It is very desirable to be able to achieve reproducible programmed heating in at least three stages for precise atomization. At the same time the actual furnace temperature should be known for the most effective atomization.

In the majority of currently available furnace systems, the programmed heating is achieved by the control of an electrical quantity (current, voltage or power) using a feedback system (Montaser and Crouch (1975)). This approach has severe deficiencies, mainly because a variety of parameters are involved in relating an electrical quantity to a furnace temperature. The temperature readout in these systems does not express the true furnace temperature. If a parameter more closely related to the furnace temperature, such as the radiation emitted is monitored and used in a feedback system, better temperature control results (Lundgren, Lundmark and Johansson (1974)); however, it still does not represent a means of direct temperature control.

The present invention is based on monitoring thermal expansion of the furnace and its use in a feedback control system for controlling the power delivered to the furnace. The thermal expansion is directly related to temperature by a well known expression:

$$\Delta l = l_0 \alpha \Delta t$$

where
 $\Delta l$ = change in length of heated material
 $l_0$ = the length of material at the initial temperature
 $\alpha$ = coefficient of linear expansion
 $\Delta t$ = change in temperature
and is therefore the basis of a direct measure of the furnace temperature.

The invention thus consists in an apparatus for controlling the power delivered to an electrically heated furnace atomiser for use in atomic spectroscopy and thus controlling the temperature of the furnace, consisting of means moveable in response to dimensional changes of the furnace due to thermal expansion and contraction connected to the body of the furnace, means converting movement of said last mentioned means to electrical signals and feedback control means arranged to control the electrical input to the furnace in response to said electrical signals.

The invention further consists in a method of measuring and controlling the temperature of an electrically heated furnace atomiser for use in atomic spectroscopy comprising monitoring thermal expansion of the furnace and utilising changes in thermal expansion to control feedback means arranged to control the electrical input to the furnace.

Figure 2:
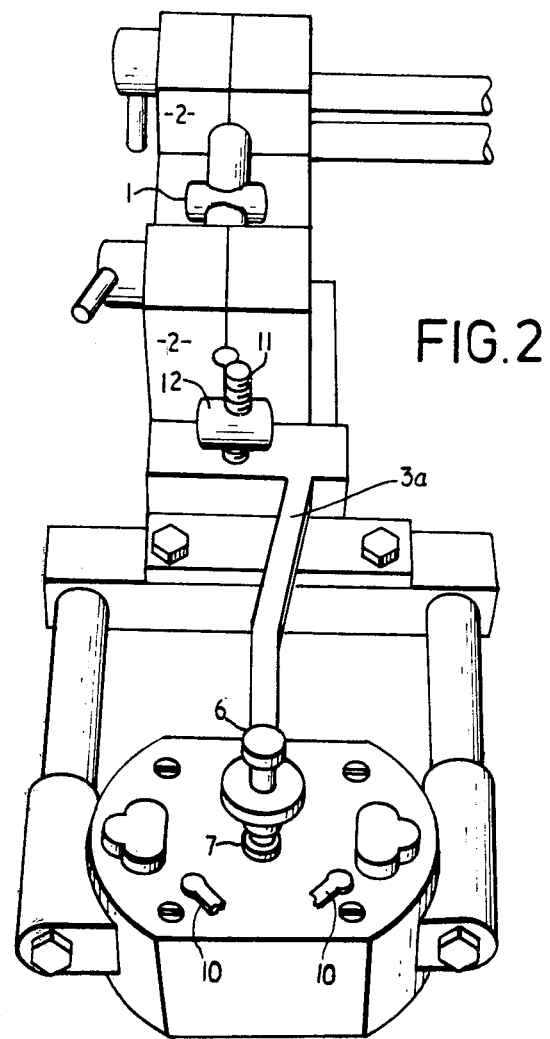

In order that the nature of the invention may be better understood a preferred form thereof is hereinafter described, by way of example, with reference to the accompanying diagrammatic drawings in which:

FIGS. 1, and 2 are diagrammatic drawings of a furnace to which the present invention is applied.

Typical furnaces to which the invention may be applied are the Perkin-Elmer HGA2100 atomiser manufactured by Perkin Elmer Corporation, Norwalk Conn., U.S.A. and Varian Techtron CRA63 carbon rod atomiser manufactured by Varian Techtron Pty. Ltd., Springvale, Victoria, Australia. Although the invention will be hereinafter described in more detail in relation to the latter of these particular furnace systems, it is to be understood that it is also applicable to other forms of furnaces. In both systems the thermal expansion of the furnace during heating is transmitted to the movement of a spring-loaded block. This block may be connectd to a suitable mechanical-to-electrical transducer or any other device capable of converting the movement into an electrical signal suitable for feedback control. Uni Measure/80 (manufactured by Uni Measure, Pasadena Calif., U.S.A.) is an example of a suitable mechanical-to-electrical transducer. Displacement of the movable steel shaft of Uni Measure/80 connected to the spring loaded furnace block, is converted very accurately to a resistance change (transducer sensitivity 200 ohms per mm; repeatability better than 0.01 ohms). The resistance change is used to operate the feedback control system using well known principles. Temperature calibration of the furnace system is carried out using thermocouples for the lower temperature range and a radiation thermometer for the higher temperature range. Once the furnace system is calibrated, precise temperature measurement and control is possible with all new (replacement) furnaces constructed of the same material.

In the drawing the graphite furnace of a Varian Techtron CRA63 is indicated at 1, this is flanked by electrode support blocks 2, the right hand block 2 being supported on a block 3 which is pivoted at 4 and supported by the coil spring 5. It is movement of block 3 about the pivot 4 produced by dimensional changes in the furnace assembly due to changes of temperature that is used to control the power supplied to the furnace.

The block 3 is connected by means of a projecting arm 3a and the adjusting screw 6 to the shaft 7 of a Uni Measure/80 mechanical-to-electrical transducer 8 connected to a feedback control system 9, through the cables 10, for controlling electrical power fed to the furnace. The power supply and control system are not shown in detail as these are of conventional design.

A lever 11 connected to an eccentric cam 12 are parts of the furnace assembly and are used in setting up the apparatus initially.

A particular advantage of the invention as applied to the particular furnace illustrated is the simplicity with which it may be incorporated in existing furnaces in that provision for movement of the right hand electrode support block 2 and the pivoted block 3 are a standard part of the furnace and it is thus only necessary to provide mechanical means to transfer the movement of the block 3 produced by temperature changes in the furnace to a suitable transducer, the electrical output for which can be readily used as a feedback control for the temperature of the furnace in a number of ways obvious to those skilled in the art.

Although the invention has been described above with reference to a preferred embodiment and drawing, it will be appreciated that numerous variations, modifications or alternatives may be substituted for specifically described features, without departing from the spirit or scope of the invention as broadly described.

To the best of the applicant's knowledge the state of the art is as described in the papers referred to, details of publication of which are as follows:

Syty, A., CRC Rev. Anal. Chem., 4(2), 155 (1974). Montaser A. and Crouch, S. R., Anal Chem., 47, 38 (1975). Lundgren, G., Lundmark, L. and Johansson, G., Anal. Chem., 46, 1028 (1974).

As pointed out above the present invention is distinguished from these disclosures by the provision of a means of direct and thus more precise temperature control of the furnace.

We claim:

1. Apparatus for controlling the power delivered to an electrically heated furnace atomiser for use in atomic spectroscopy and thus controlling the temperature of the furnace, consisting of means moveable to a plurality of different positions in response to dimensional changes of the furnace due to thermal expansion and contraction connected to the body of the furnace, means for converting movement of said last-mentioned means to a plurality of respective electrical signals and feedback control means arranged to control the electrical input to the furnace in response to said electrical signals.

2. A method of measuring and controlling a wide range of temperature of an electrically heated furnace atomiser for use in atomic spectroscopy comprising: continuously monitoring thermal expansion of the furnace and utilising changes in thermal expansion to continuously control feedback means arranged to control the electrical input to the furnace.

* * * * *